United States Patent [19]
Schlichting et al.

[11] Patent Number: 5,532,393
[45] Date of Patent: Jul. 2, 1996

[54] PROCESS OF PREPARING WAX ESTER

[75] Inventors: Eberhard Schlichting, Wehrheim; Henning Buchold; Gerd Mallok, both of Hanau; Fritz-Jürgen Gärtner, Bickenbach; Hans-Martin Stönner, Eschborn, all of Germany

[73] Assignee: Metallgesellschaft Aktiengesellschaft, Frankfurt, Germany

[21] Appl. No.: 358,447

[22] Filed: Dec. 16, 1994

[30] Foreign Application Priority Data

Dec. 18, 1993 [DE] Germany .......................... 43 43 320.0

[51] Int. Cl.⁶ ..................................................... C11C 3/00
[52] U.S. Cl. .......................................... 554/170; 554/167
[58] Field of Search ..................................... 554/167, 170

[56] References Cited

FOREIGN PATENT DOCUMENTS 2503195  7/1976  Germany .

OTHER PUBLICATIONS

Perlstein et al., Journal of the Am. Chem. Soc., 1974, vol. 51, No. 8, pp. 335–339, "Synthesis of wax esters for use as possible sperm oil replacements".

*Primary Examiner*—José G. Dees
*Assistant Examiner*—Deborah D. Carr
*Attorney, Agent, or Firm*—Sprung Horn Kramer & Woods

[57] ABSTRACT

The wax ester is prepared from a liquid mixture which contains at least one fatty acid and at least one fatty alcohol. The fatty acid and the fatty alcohol contain 6 to 30 carbon atoms per molecule. The mixture is agitated at temperatures in the range from about 105° to 300° C. and is sprayed into a spraying zone. An atmosphere which contains water vapor is formed in the spraying zone and is removed at least in part. The mixture of fatty acid and fatty alcohol may be agitated in at least one stirred vessel preceding the spraying zone. A catalyst is preferably not added.

7 Claims, 1 Drawing Sheet

PROCESS OF PREPARING WAX ESTER

DESCRIPTION

This invention relates to a process of preparing wax ester from a liquid mixture which comprises at least one fatty acid and at least one fatty alcohol, wherein the fatty acid and the fatty alcohol contain 6 to 30 carbon atoms per molecule.

A process of that kind has been described in the periodical JAOCS, volume 69, No. 11 (November 1992), pages 1150 to 1153. In accordance therewith the mixture of fatty acid and fatty alcohol is stirred at temperatures in the range from 150 to 275° C. together with a zeolite catalyst in a laboratory apparatus.

It is an object of the invention to carry out the above-mentioned process on a commercial scale in a simple manner. This is accomplished in accordance with the invention in that the mixture is agitated at temperatures in the range from about 105 to 300° C. and is sprayed into a spraying zone and an atmosphere which contains water vapor is formed in the spraying zone and is withdrawn at least in part. The agitation and the resulting intense mixing of the reactants may be effected, e.g., by stirring or circulating. The circulation may be effected with a considerable turbulence, e.g., by a suitable conducting of the flow and/or by a supply if inert gas.

Even though the process may be accelerated by the addition of a catalyst, the process in accordance with the invention may also be carried out without a catalyst. The latter processing will be preferred because in a preparation of wax ester on a commercial scale the omission of a catalyst will greatly reduce the costs.

Particularly in a processing without a catalyst, it will be desirable to maintain the mixture at temperatures of at least 120° C. during the agitation and spraying.

The process may be carried out continuously or in batches. For a continuous processing it is recommendable to mix the fatty acid and the fatty alcohol in a first reaction zone to form a mixture which contains a wax ester and which is passed through at least one further reaction zone, in which the mixture is agitated, and the mixture is sprayed in at least one spraying zone.

In the process in accordance with the invention it is important that the water vapor formed by the esterification is withdrawn at least in part from the reaction mixture. This may be effected in various ways, e.g., in that the atmosphere which contains water vapor is sucked off over the mixture. Alternatively, an inert gas, such as nitrogen, may be passed through the mixture to effect a stripping so that the inert gas entrains water molecules from the liquid mixture as well as from the spraying zone.

It is recommended to inject the mixture into the spraying zone in the form of small droplets which preferably have a diameter in the range from 0.01 to 5.0 mm.

The ratio of fatty acid to fatty alcohol at the beginning of the reaction may be varied in a wide range. To prepare a product which is rich in wax ester and contains only small residual amounts of fatty acid and fatty alcohol, fatty acid and fatty alcohol will be supplied at a mole ratio of 1:1. If it is desired to minimize the acid content of the wax ester product, it will be recommendable to begin with an excess of fatty alcohol. In this way it is readily possible to prepare wax esters having an acid value below 1 or even below 0.3. The acid value is measured in the usual manner in mg KOH required per gram of the sample which is examined for a neutralization of the residual acid.

BRIEF DESCRIPTION OF DRAWINGS

Further features of the process will be explained with reference to the drawing, in which.

Figure 1:
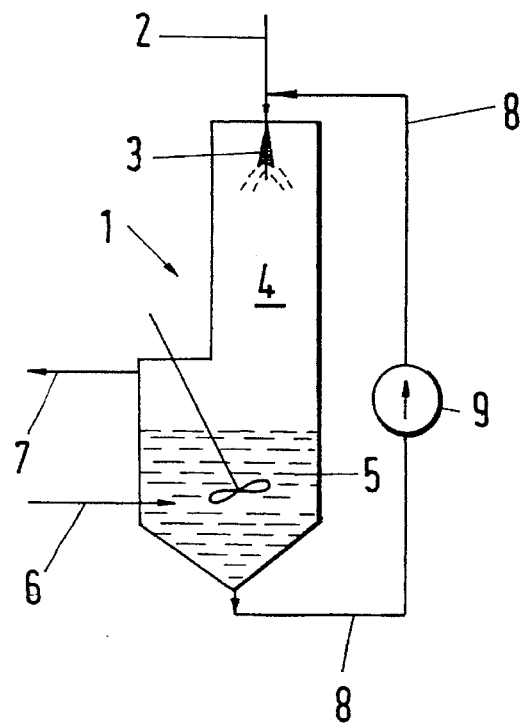
FIG. 1 illustrates a single-stage procedure, which is particularly suitable for batchwise operation.

In the process of FIG. 1 a fatty acid and fatty alcohol are jointly supplied to a reactor 1 through a line 2 and the mixture is sprayed in the form of fine droplets through a nozzle 3 into the spraying zone 4 of the reactor 1. Below the spraying zone 4 the reactor 1 contains a reaction zone 5, in which the mixture of fatty acid, fatty alcohol and the resulting wax ester is continuously stirred intensely. An inert gas, such as nitrogen, is introduced into the mixture through line 6. The reaction of fatty acid with fatty alcohol at the temperatures in the range from 105° to 300° C. and preferably of at least 120° C. prevailing in the reactor results in the formation of water vapor, which is effectively separated from the reaction mixture mainly by the spraying. The resulting water vapor together with the inert gas is withdrawn from the reactor 1 in line 7, e.g., by being sucked off. Any starting material and wax ester product which is entrained may be recovered in a manner known per se by condensation and may then be recycled to the reactor 1.

The liquid which accumulates in the reaction zone 5 contains starting material and wax ester and is circulated for a certain time and by means of a pump 9 is fed in line 8 to the top of the reactor 1 and is then sprayed again through the nozzle 3. During a batchwise operation of the reactor the residence times in the reactor are about 1 to 10 hours and the total amount of liquid is sprayed 1 to 20 times per hour.

Figure 2:
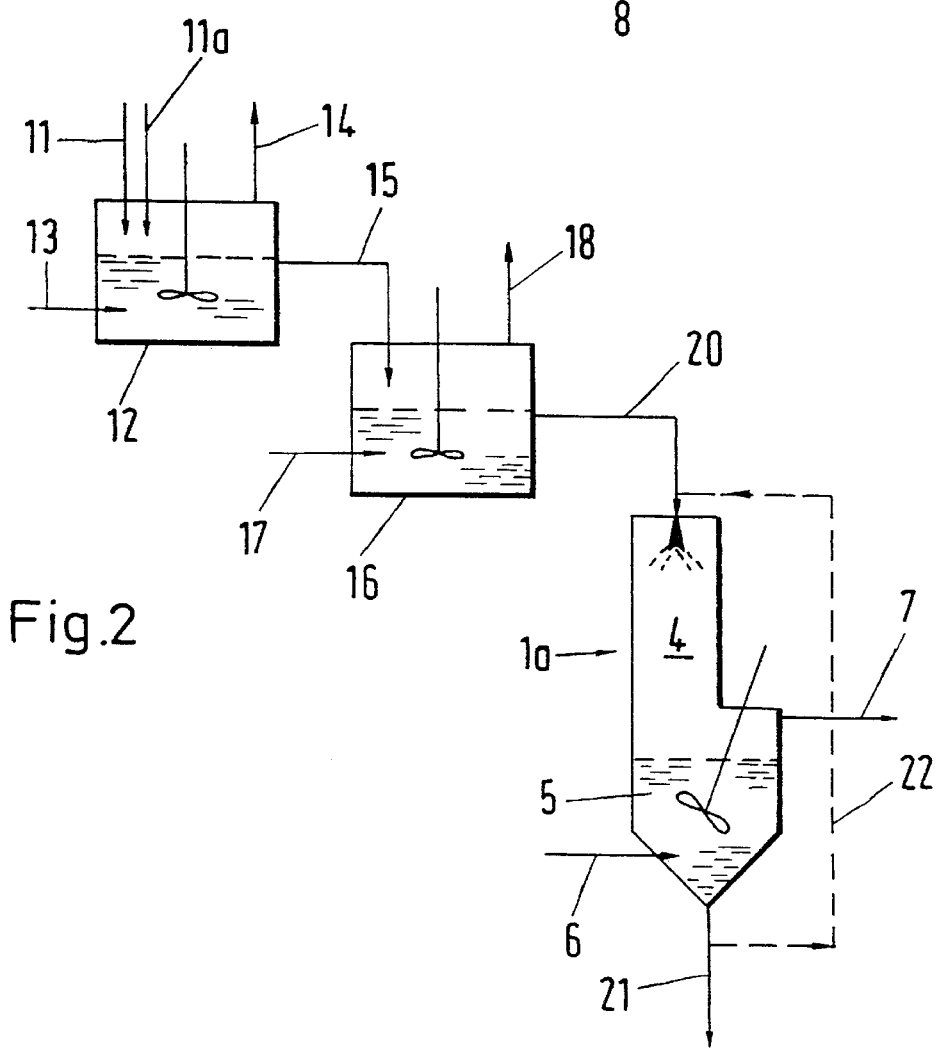
FIG. 2 illustrates a three-stage procedure, which is particularly suitable for continuous operation.

Just as the process of FIG. 1, the process shown in FIG. 2 may be carried out without a catalyst. In accordance with FIG. 2, a first reaction vessel 12 is supplied with fatty acid through line 11 and with fatty alcohol through a line 11a. The mixture is intensely stirred in the first reaction vessel 12. During the stirring, an inert gas, such as nitrogen, is supplied through line 12. Inert gas which contains water vapor is withdrawn through a line 14. Because only a partial reaction is effected in the first reaction vessel 12, a liquid containing fatty acid, fatty alcohol, and wax ester is withdrawn in a line 15 and supplied to a second reaction vessel 16. That second vessel 16 is basically operated like the first reaction vessel 12 and is also provided with an inert gas supply line 7 and a line 8 for withdrawing gas which contains water vapor.

A liquid which is withdrawn in line 20 from the second reaction vessel 16 has a higher content of wax ester than the liquid in line 15 and contains also residual fatty acid and residual fatty alcohol. That liquid is supplied to a reactor 1a, which, as has been explained with reference to FIG. 1, contains a spraying zone 4 and a reaction zone 5. Inert gas is supplied through a line 6 and gas which contains water vapor is withdrawn in line 7. A product which is rich in wax ester becomes available in line 21. In case of need the reactor 1a may also be operated with a circulation of liquid in that part of the liquid is recycled through a line 21 to the top of the reactor 1a in a line 22, which is indicated by a broken line. In the continuous process illustrated in FIG. 2 the total residence time is usually longer than the residence time used in the batchwise operation of FIG. 1.

The process illustrated in FIG. 2 may be modified in that only one reaction vessel is employed or more than two reaction vessels are used. Besides, more than one reactor provided with spraying means may be employed.

EXAMPLE 1

A batchwise operation as illustrated in FIG. 1 is carried out on a laboratory scale. A reactor 1 comprising an electrically heatable jacket is employed. The reactor is charged with 208 g of a mixture of fatty acids containing 8 to 18 carbon atoms per molecule and having an average molecular weight of 208 and with 1.1 moles of a fatty alcohol having 16 carbon atoms per molecule. The reactants are at a temperature of 65° C. The acid value of the mixture is 117 mg KOH/g. The interior of the reactor is at a temperature of 250° C. Nitrogen as an inert gas is supplied through line 6.6 liters liquid per hour are sprayed through the nozzle in the form of droplets from 0.01 to 1.0 mm into the spraying zone 4. In a control experiment that spraying and the line 8 are omitted. The progress of the esterifying reaction is monitored once per hour in that the acid value is measured. The results are as follows:

| Time of reaction hours | 0 | 1 | 2 | 3 | 4 | 5 | 6 |
|---|---|---|---|---|---|---|---|
| Acid value with spraying | 117 | 7.7 | 0.49 | 0.12 | | | |
| Acid value without spraying | 117 | 11.4 | 6.4 | 4.2 | 3.1 | 2.33 | 1.68 |

In the processing in accordance with the invention with spraying the experiment can be terminated after 3 hours because a virtually complete esterification has been effected. The control experiment without spraying is terminated with an unsatisfactory result after the reaction mixture has constantly been stirred for six hours.

EXAMPLE 2

For a continuous processing as shown in FIG. 2 on a laboratory scale, three stirred vessels 2, 16, and 1a are used which had electrically heatable jackets. The vessel 1a of the final stage comprises a spraying zone 4 and is provided with a recycle line 22. The first stirred vessel 12 is supplied through line 11 with the mixture of fatty acids having 8 to 18 carbon atoms which has also been used in Example 1 and is supplied through line 11a with a fatty alcohol having 12 carbon atoms. 1.2 moles fatty alcohol per mole of fatty acid mixture are supplied, the reactants had been preheated to 200° C. A temperature of 250° C. is maintained in each stirred vessel and each vessel is supplied with nitrogen as an inert gas. The residence time in the stirred vessels is 4 hours.

The acid values 21.2, 3.8, and 0.2 are measured in lines 15, 20, and 21, respectively, which means that the product in line 21 is virtually free of acid. But if the spraying zone 4 and the recycle line 21 are not used in the final stage and the reactor 1a is operated only as a stirred vessel, a product is obtained which has an acid value of 2.1, which means that the wax ester product has still a considerable residual acid content.

We claim:

1. A process of preparing wax ester from a liquid mixture which consists essentially of at least one fatty acid and at least one fatty alcohol, wherein the fatty acid and the fatty alcohol contain 6 to 30 carbon atoms per molecule, which comprises agitating the mixture at temperatures in the range from about 105° to 300° C., spraying said mixture into a spraying zone thereby forming water vapor in the spraying zone, and withdrawing the water vapor from said zone at least in part.

2. A process according to claim 1, wherein the mixture is maintained at temperatures of at least 120° C. as it is agitated and sprayed.

3. A process according to claim 1, wherein the fatty acid and the fatty alcohol are mixed in a first reaction zone to form a mixture which contains a wax ester, the mixture is passed through at least one further reaction zone, wherein the mixture is agitated, and the mixture is then sprayed in at least one spraying zone.

4. A process according to claim 1, wherein the mixture is agitated and sprayed without addition of a catalyst.

5. A process according to claim 1, wherein an inert gas is introduced into the mixture as it is agitated and inert gas which contains water vapor is withdrawn from the mixture.

6. A process according to claim 1, wherein the water vapor formed during the reaction is sucked off over the mixture.

7. A process according to claim 1, wherein an excess of fatty alcohol is maintained in the mixture and a product which is rich in wax ester and is virtually free of acid is prepared.

* * * * *